United States Patent [19]

Nishimura et al.

[11] 4,405,743

[45] Sep. 20, 1983

[54] PYRAZOLYLPYRIMIDINE DERIVATIVES

[75] Inventors: Tamio Nishimura, Sagamihara; Yoshiko Miyamoto, Kawasaki; Hiroshi Ohyama, Chigasaki; Hiroshi Yamamura, Oiso; Ken Morita, Atsugi; Kuniomi Matsumoto, Machida; Tetsuro Watanabe, Yokohama, all of Japan

[73] Assignees: Hokko Chemical Industry Co., Ltd.; Meiji Seika Kaisha Ltd., both of Tokyo, Japan

[21] Appl. No.: 311,655

[22] Filed: Oct. 15, 1981

Related U.S. Application Data

[63] Continuation of Ser. No. 71,691, Aug. 31, 1979, abandoned.

[51] Int. Cl.³ .................. A61K 31/505; C07D 403/04
[52] U.S. Cl. .................... 424/321; 544/320; 544/321; 544/331
[58] Field of Search .......... 544/321; 424/251

[56] References Cited

U.S. PATENT DOCUMENTS 2,584,024  1/1952  Kaczka et al. ............ 544/320
3,040,047  6/1962  Sirakawa .................. 544/320
3,723,433  3/1973  Ueno et al. ............... 544/321

FOREIGN PATENT DOCUMENTS 1220428  7/1966  Fed. Rep. of Germany ...... 544/320
39-4491  4/1964  Japan .
39-4492  4/1964  Japan .................................. 544/320
39-4493  4/1964  Japan .
48-72176  9/1973  Japan .................................. 544/320

OTHER PUBLICATIONS

Nishimura et al., "ACS/CSJ Chemical Congress; Abstracts", 1979 Abstract #78.

Primary Examiner—Donald G. Daus
Assistant Examiner—James H. Turnipseed
Attorney, Agent, or Firm—Abelman, Frayne & Rezac

[57] ABSTRACT

The present invention relates to pyrazolylpyrimidine derivatives of the formula

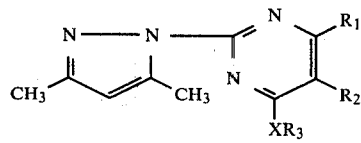

wherein X, $R_1$, $R_2$ and $R_3$ are as herein defined. These compounds are useful as fungicides in agriculture and horticulture.

2 Claims, No Drawings

PYRAZOLYLPYRIMIDINE DERIVATIVES

This is a continuation of application Ser. No. 071,691 filed Aug. 31, 1979, now abandoned.

This invention relates to novel pyrazolylpyrimidine derivatives of the following general formula (I)

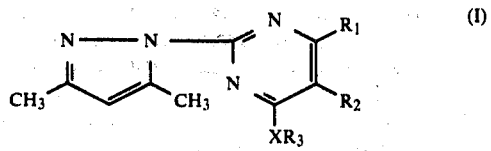

(in which $R_1$ is a hydrogen atom or an alkyl group, $R_2$ is a hydrogen atom or a $C_{1-4}$ alkyl group, X is an oxygen atom or a sulfur atom, and $R_3$ is a lower alkyl group, a phenyl group or a substituted phenyl group provided that when $R_1$ is an alkyl group, $R_2$ is a $C_{1-4}$ alkyl group and X is a sulfur atom, $R_3$ is an ethyl group, or when $R_1$ is an alkyl group, $R_2$ is a hydrogen atom and X is an oxygen atom, $R_3$ is a substituted phenyl group). Further, this invention relates to fungicides useful for agriculture and horticulture, comprising at least one of said pyrazolylpyrimidine derivatives.

Several compounds similar to those of the above formula (I) are known including 2-(3,5-dimethyl-1-pyrazolyl)-4-methyl-6-hydroxypyrimidine, 2-(3,5-dimethyl-1-pyrazolyl)-4-phenyl-6-hydroxypyrimidine and 2-(3,5-dimethyl 1-pyrazolyl)-4-methyl-6-thiocyanopyrimidine. According to the Annual Report of the Takeda's Research Institute, Vol. 24, pages 250-258 (1965), these known compounds show an activity of controlling rice blast but exhibit a violent chemical injury.

During the course of our investigation, we have prepared a number of pyrazolylpyrimidine compounds and tested their practicability as a fungicide for agriculture and horticulture. As a result, it has been found that the compounds of the above-mentioned general formula (I) are novel and, when applied as an agricultural and horticultural fungicide, show an extremely high control activity, particularly, against rice blast, rice brown spot, cucumber powdery mildew and the like. Aside from rice blast (*Pyricularia oryzae*), rice brown spot (*Cochliobolus miyabeanus*) and cucumber powdery mildew (*Sphaerotheca fuliginea*), these compounds highly act on various plant pathogens and particularly molds and thus snow high control effects on grape ripe rot (*Glomerella cingulata*), citrus melanose (*Diaporthe citri*), chestnut blight (*Endothia parasitica*), cucumber gummy stem blight (*Mycosphaerell melonis*), kidney bean stem rot (*Sclerotinia sclerotiorum*), apple brown rot (*Sclerotinia fructigena*), rice sheath blight (*Pellicularia sasakii*), citrus common green mold (*Penicillium digitatum*), cucumber gray mold (*Botrytis cinerea*), barley stripe (*Helminthosporium gramineum*), black belly rice kernel (*Alternaria padwikii, Curvularia sp.*), rice leaf spot (*Fusarium nivale*), cabbage black leg (*Phoma lingam*), eggplant damping off disease (*Rhizootonia solani*) and the like.

A series of these compounds according to the invention show a high fungicidal action but do not give any chemical injury against useful plants. In addition, the compounds do not exhibit any toxicity against men and animals or fishes and are thus usable safely and very excellent as a fungicide.

These features of the invention are considered not to be known from the technical level as stated in the above-mentioned literature even to those skilled in the art. The new compounds according to the invention are highly practical as an all-round fungicide for agriculture and horticulture.

The preparation of the compounds according to the invention will be particularly described.

The compounds of the formula (I) can be prepared according to the following reaction formula:

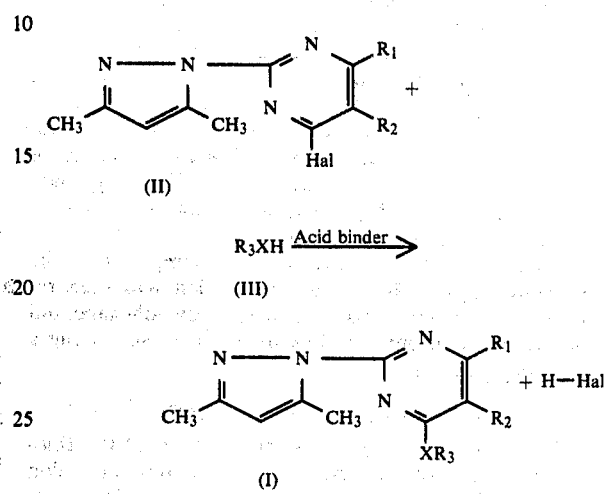

(in which $R_1$, $R_2$, $R_3$ and X have the same meanings as defined hereinbefore, respectively).

The compound of the formula (II) is readily obtainable by reacting a corresponding 6-hydroxy compound with phosphorus oxychloride by a usual manner, as described in Japanese Patent Publication No. 39-4493.

The reaction of the compound of the formula (II) and the compound of the formula (III) is feasible without use of any solvent but is ordinarily preferable to be conducted in a solvent. In some cases, the compound of the formula (III) may be usable as a solvent, but usually employed solvents include organic solvents such as hydrocarbons, halogenated hydrocarbons, ethers, esters, acid amides, alcohols, dimethylsulfoxide and the like, and water. In order to carry out the reaction smoothly, it is preferable to use an acid binder. Examples of such acid binder include organic amines such as triethylamine, pyridine and the like, inorganic bases such as potassium carbonate, sodium hydroxide and the like, and metallic sodium, metallic potassium, sodium alkoxide, potassium alkoxide, sodium hydride, sodium amide and the like. The compound of the formula (III) may be reacted in advance with the acid binder and then isolated, for example, as a sodium salt, followed by reacting further with the compound of the formula (II).

Though the reaction proceeds at room temperature, it is preferred to effect the reaction under heating conditions so as to shorten the reaction time. The reaction time varies depending on the kind of the compound of the formula (III), and the solvent and reaction temperature employed, but the reaction is completed within the short period of time when using a polar solvent. After completion of the reaction, the salt of the acid binder which have precipitated in the reaction solution are removed by filtration and then the solvent is removed by distillation from the filtrate to obtain the compound of the invention. Alternatively, to the reaction mixture may be added with a mixture of a solvent such as benzene, chloroform, ether, tetrahydrofuran or the like with water to obtain an intended compound by extraction.

The synthesis of the compounds according to the invention will be particularly described in the following examples 1-6.

Example 1 (Preparation of Compound No. 4)

20.9 of 2-(3,5-dimethyl-1-pyrazolyl)-6-chloropyrimidine, 11.0 g of thiophenol, 13.8 g of anhydrous potassium carbonate and 100 ml of dimethylsulfoxide were placed in a 300 ml flask and agitated at 80° C. for 1 hour. After cooling, benzene and water were added to the reaction system and the organic layer was collected. The organic layer was dried with anhydrous sodium sulfate and distilled under reduced pressure to remove the solvent thereby obtaining 26.8 g of the captioned compound as a light yellow oily substance with a refractive index, $n_D^{20}$, of 1.6284.

When allowed to stand at room temperature, the substance gradually crystallized, which was then recrystallized from a mixed solvent of cyclohexane and carbon tetrachloride to obtain white crystals having a melting point of 75°–77° C.

Example 2 (Preparation of Compound No. 27)

Example 1 was repeated using, instead of the thiophenol, 12.2 g of 2,4-dimethylphenol thereby obtaining 29.9 g of the captioned compound as light yellow crystals. The compound was recrystallized from cyclohexane to obtain white crystals having a melting point of 92.5°–93.5° C.

Example 3 (Preparation of Compound No. 21)

22.3 g of 2-(3,5-dimethyl-1-pyrazolyl)-4-methyl-6-chloropyrimidine, 18.4 g of sodium m-trifluoromethylphenolate and 100 ml of dimethylformamide were charged into a 300 ml flask and agitated at 80° C. for 3 hours. After cooling, benzene and water were added to the reaction system and the organic layer was taken out. The organic layer was dried with anhydrous sodium sulfate and the solvent was removed by distillation under reduced pressure to obtain 32 g of the captioned compound as light yellow crystals. The compound was recrystallized from a mixed solvent of cyclohexane and acetone to obtain white crystals having a melting point of 117°–118° C.

Example 4 (Preparation of Compound No. 32)

100 ml of absolute ethanol was placed in a 300 ml flask, to which was added 2.3 g of metallic sodium for reaction. Then, 22.3 g of 2-(3,5-dimethyl-1-pyrazolyl)-5-methyl-6-chloropyrimidine was added to the reaction system and agitated at room temperature for 1 hour. The resulting salt was removed by filtration and the filtrate was concentrated to obtain 22.3 g of the captioned compound as white crystals. The compound was recrystallized from hexane to obtain white crystals having a melting point of 78°–79° C.

Example 5 (Preparation of Compound No. 41)

Example 4 was repeated using 27.9 g of 2-(3,5-dimethyl-1-pyrazolyl)-4-methyl-5-n-butyl-6-chloropyrimidine instead of the 2-(3,5-dimethyl-1-pyrazolyl)-5-methyl-6-chloropyrimidine thereby obtaining 26.8 g of the captioned compound as light yellow crystals. The compound was recrystallized from a mixed solvent of cyclohexane and carbon tetrachloride to obtain crystals having a melting point of 59°–61° C.

Example 6 (Preparation of Compound No. 42)

27.9 g of 2-(3,5-dimethyl-1-pyrazolyl)-4-methyl-5-n-butyl-6-chloropyrimidine, 7.0 g of ethyl mercaptan, 13.8 g of anhydrous potassium carbonate and 150 ml of dimethylsulfoxide were charged into a 300 ml flask, followed by agitating at 40° C. for 8 hours. After cooling, benzene and water were added to the reaction system and the organic layer was taken out. The organic layer was dried with anhydrous sodium sulfate and the solvent was removed by distillation under reduced pressure to obtain 27.1 g of the captioned compound as a light yellow oily substance. This compound had a refractive index, $n_D^{20}$, of 1.5718.

The compounds of the general formula (I) as prepared in the above examples are shown in Table 1 below.

TABLE 1

| Compound No. | $R_1$ | $R_2$ | X | $R_3$ | Refractive Index or m.p. |
|---|---|---|---|---|---|
| 1 | H | H | O | $C_2H_5$ | $n_D^{20}$ 1.5450 |
| 2 | H | H | S | $C_2H_5$ | m.p. 44–47 |
| 3 | H | H | O |  | $n_D^{20}$ 1.5982 |
| 4 | H | H | S |  | $n_D^{20}$ 1.6284 |
| 5 | $CH_3$ | H | S |  | m.p. 112–114 |
| 6 | $CH_3$ | H | O |  | m.p. 144.5–145 |
| 7 | $CH_3$ | H | O |  | m.p. 114.5–115 |
| 8 | $CH_3$ | H | O |  | m.p. 162–163 |
| 9 | $CH_3$ | H | O |  | m.p. 107–108 |
| 10 | $CH_3$ | H | O |  | m.p. 158.5–160 |
| 11 | $CH_3$ | H | O |  | m.p. 77–78 |
| 12 | $CH_3$ | H | O |  | m.p. 82.5–83 |
| 13 | $CH_3$ | H | O |  | m.p. 92–93 |
| 14 | $CH_3$ | H | O |  | m.p. 94–95 |

TABLE 1-continued

| Compound No. | R₁ | R₂ | X | R₃ | Refractive Index or m.p. |
|---|---|---|---|---|---|
| 15 | $CH_3$ | H | O | -C₆H₄-C₄H₉-t | m.p. 124.5–125 |
| 16 | $CH_3$ | H | S | -C₆H₄-CH₃ | $n_D^{20}$ 1.6380 |
| 17 | $CH_3$ | H | O | -C₆H₄-OCH₃ | m.p. 107.5–108.5 |
| 18 | $CH_3$ | H | O | -C₆H₄-SCH₃ | m.p. 124–125 |
| 19 | $CH_3$ | H | O | -C₆H₄-CN | m.p. 173–174 |
| 20 | $CH_3$ | H | O | -C₆H₄-NO₂ | m.p. 166–167 |
| 21 | $CH_3$ | H | O | -C₆H₄-CF₃ | m.p. 117–118 |
| 22 | $CH_3$ | H | O | -C₆H₄-COOC₂H₅ | m.p. 109–109.5 |
| 23 | $CH_3$ | H | O | -C₆H₃(Cl)(Cl) | m.p. 199–200 |
| 24 | $CH_3$ | H | O | -C₆H₃(Cl)(Cl) | m.p. 156–157 |
| 25 | $CH_3$ | H | O | -C₆H₂(Cl)(Br)(Cl) | m.p. 209–210 |
| 26 | $CH_3$ | H | O | -C₆H₃(CH₃)(Cl) | m.p. 123–124 |
| 27 | $CH_3$ | H | O | -C₆H₃(CH₃)(CH₃) | m.p. 92.5–93.5 |
| 28 | $CH_3$ | H | O | -C₆H₃(CH₃)(CH₃) | $n_D^{20}$ 1.5821 |
| 29 | $CH_3$ | H | O | -C₆H₃(CH₃)(CH₃) | m.p. 97.5–98 |
| 30 | $CH_3$ | H | O | -C₆H₂(CH₃)(CH₃)(CH₃) | m.p. 75–76.5 |
| 31 | $CH_3$ | H | O | -C₆H₃(CH₃)(NO₂) | m.p. 142–143 |
| 32 | H | $CH_3$ | O | $C_2H_5$ | m.p. 78–79 |
| 33 | H | $CH_3$ | S | $C_2H_5$ | m.p. 58–59 |
| 34 | H | $CH_3$ | O | -C₆H₅ | m.p. 117–118.5 |
| 35 | H | $CH_3$ | S | -C₆H₅ | m.p. 131–132 |
| 36 | $CH_3$ | $CH_3$ | O | $C_2H_5$ | m.p. 90–92 |
| 37 | $CH_3$ | $CH_3$ | S | $C_2H_5$ | m.p. 59–61.5 |
| 38 | $CH_3$ | $CH_3$ | O | -C₆H₅ | $n_D^{20}$ 1.6035 |
| 39 | $CH_3$ | $CH_3$ | S | -C₆H₅ | $n_D^{20}$ 1.6505 |
| 40 | $CH_3$ | n-C₃H₇ | O | $CH_3$ | m.p. 62–65 |
| 41 | $CH_3$ | n-C₄H₉ | O | $C_2H_5$ | m.p. 59–61 |
| 42 | $CH_3$ | n-C₄H₉ | S | $C_2H_5$ | $n_D^{20}$ 1.5718 |
| 43 | $CH_3$ | n-C₄H₉ | O | -C₆H₅ | m.p. 97.5–99.5 |
| 44 | $CH_3$ | n-C₄H₉ | S | -C₆H₅ | m.p. 85–88 |
| 45 | n-C₆H₁₃ | H | S | $C_2H_5$ | $n_D^{20}$ 1.5549 |
| 46 | n-C₆H₁₃ | H | S | -C₆H₅ | $n_D^{20}$ 1.6286 |
| 47 | n-C₆H₁₃ | H | O | -C₆H₄-Cl | m.p. 83–85 |

In order to apply the compounds according to the invention to control plant diseases of agricultural and horticultural crops, the compounds may be used as they are or may be diluted with a suitable carrier such as water or a solid powder, to which an adjuvant such as a spreader is added, if necessary. Alternatively, the compounds may be mixed with various types of liquids or solid carriers as is ordinarily carried out for the preparation of agricultural chemicals. If necessary, adjuvants such as a wetting agent, a spreader, a dispersing agent, an emulsifier, a binder and the like may be added to the mixture for use as various types of preparations such as wettable powders, solutions, emulsions, dusts, granules, fine granules.

In preparing these chemicals, there are used as a liquid carrier water, aromatic hydrocarbons, aliphatic hydrocarbons, alcohols, esters, ketones, and highly polar solvents such as dimethylformamide, dimethylsulfoxide and the like; as a solid carrier mineral powders such as clay, talc, kaolin, bentonite, diatomaceous earth, silicic acid and the like, and organic powders such as wood meal; and as an adjuvant nonionic, anionic, cationic and amphoteric surface active agents, ligninsulfonic acid or its salts, gums, fatty acid salts, pastes such as of methyl cellulose, and the like.

The agricultural and horticultural fungicide according to the invention can be applied directly to plants to be controlled. Alternatively, it may be applied to the habitat of a plant such as a water surface or a soil surface, if necessary, or may be used by incorporation into soil. When the fungicide of the invention is used as a liquid form, it is preferred to contain the compound of the invention in a concentration of 10–1000 ppm in a spraying liquid. In the case of a "small amount concentrate" spray or a spray by airplane, a more concentrated liquid may be used. With the cases of a dust, a granule and a fine granule, it is preferred that the compound is contained in an amount of 0.1–30%.

The present invention will be further particularly described by way of examples dealing with agricultural and horticultural fungicides, which should not be construed as limiting thereto the invention.

Example 7 (Wettable powder)

20 parts by weight of the compound No. 2, 5 parts by weight of polyoxyethylene alkyl aryl ether, 3 parts by weight of calcium ligninsulfonate and 72 parts by weight of diatomaceous earth were uniformly milled and mixed to obtain a wettable powder containing 20% of the effective component.

Example 8 (Granule)

5 parts by weight of the compound No. 19, 1 part by weight of calcium ligninsulfonate, 30 parts by weight of bentonite and 64 parts by weight of clay were uniformly pulverized, to which was added a suitable amount of water, followed by kneading and granulating to obtain a granule containing 5 % of the effective component.

Example 9 (Dust)

3 parts by weight of the compound No. 10, 0.5 parts by weight of finely powdered silica, 0.5 parts by weight of calcium stearate, 50 parts by weight of clay and 46 parts by weight of talc were uniformly mixed to obtain a dust containing 3% of the effective component.

Example 10 (Emulsion)

20 parts by weight of the compound No. 1, 30 parts by weight of dimethylformamide, 35 parts by weight of xylene and 15 parts by weight of polyoxyethylene alkylaryl ether were uniformly mixed to obtain an emulsion containing 20% of the effective component.

Experimental Example 1 (Test For Effect of Controlling Rice Blast (Prevention))

To seedlings of a rice plant (variety: Asahi) grown up to the third leaf stage which had been soil cultured in an unglazed pot with a diameter of 9 cm in a green house was sprayed a test liquid obtained by dispersing each of wettable powders prepared as in Example 7 in a predetermined concentration. One day after the spraying, a spore suspension of Pyricularia oryzae was sprayed over the seedlings for inoculation. After the inoculation, the pot was placed in a humid chamber and maintained overnight at 24°–25° C. under conditions of relative humidity of 95–100%. Five days after the inoculation, the number of lesions per leaf of the third leaf stage was checked and a control value was calculated from the following equation. The chemical injury against the rice plant was evaluated according to the following equation. The test results are shown in Table 2.

Control Value (%) =

$$\left(1 - \frac{\text{Number of lesions in sprayed plot}}{\text{Number of lesions in non-sprayed plot}}\right) \times 100$$

Check Standard for Chemical Injury

5: Very extreme
4: Extreme
3: Fair
2: Some
1: Slight
0: Nil

TABLE 2
(Effect of controlling blast)

| Compound No. | Concentration (ppm) | Control Value (%) | Degree of chemical injury |
|---|---|---|---|
| 1 | 200 | 100 | 0 |
| 2 | " | 100 | 0 |
| 3 | " | 100 | 0 |
| 4 | " | 100 | 0 |
| 5 | " | 100 | 0 |
| 6 | " | 100 | 0 |
| 7 | " | 100 | 0 |
| 8 | " | 100 | 0 |
| 9 | " | 100 | 0 |
| 10 | " | 100 | 0 |
| 11 | " | 100 | 0 |
| 12 | " | 100 | 0 |
| 13 | " | 100 | 0 |
| 14 | " | 100 | 0 |
| 15 | " | 100 | 0 |
| 16 | " | 100 | 0 |
| 17 | " | 100 | 0 |
| 18 | " | 100 | 0 |
| 19 | " | 100 | 0 |
| 20 | " | 82 | 0 |
| 21 | " | 100 | 0 |
| 22 | " | 100 | 0 |
| 23 | " | 100 | 0 |
| 24 | " | 92 | 0 |
| 25 | " | 86 | 0 |
| 26 | " | 100 | 0 |
| 27 | " | 100 | 0 |
| 28 | " | 100 | 0 |
| 29 | " | 100 | 0 |
| 30 | " | 100 | 0 |
| 31 | " | 100 | 0 |
| 32 | " | 100 | 0 |
| 33 | " | 100 | 0 |
| 34 | " | 92 | 0 |
| 35 | " | 84 | 0 |
| 36 | " | 100 | 0 |
| 37 | " | 100 | 0 |
| 38 | " | 100 | 0 |
| 39 | " | 100 | 0 |
| 40 | " | 100 | 0 |
| 41 | " | 100 | 0 |
| 42 | " | 100 | 0 |
| 43 | " | 100 | 0 |
| 44 | " | 100 | 0 |
| 45 | " | 92 | 0 |
| 46 | " | 84 | 0 |

TABLE 2-continued (Effect of controlling blast)

| Compound No. | Concentration (ppm) | Control Value (%) | Degree of chemical injury |
|---|---|---|---|
| 47 | " | 100 | 0 |
| Comparative Chemical 1 | " | 75 | 5 |
| Comparative Chemical 2 | " | 76 | 5 |
| Comparative Chemical 3 | " | 74 | 5 |
| Comparative Chemical 4 | 480 | 76 | 0 |
| Non-treated Plot | — | 0 | — |

In the above table, the comparative chemicals 1, 2 and 3 are, respectively, wettable powders prepared as in Example 7 and containing 2-(3,5-dimethyl-1-pyrazolyl)-4-methyl-6-hydroxypyrimidine, 2-(3,5-dimethyl-1-pyrazolyl)-4-phenyl-6-hydroxypyrimidine and 2-(3,5-dimethyl-1-pyrazolyl)-4-methyl-6-thiocyanopyrimidine, and the comparative chemical 4 is a commercially available fungicide (under the trade name of Kitazin P emulsion) which contains O,O-diisopropyl-S-benzyl-phosphorothiolate.

Experimental Example 2 (Test for Effect of Controlling Rice Blast (Cure))

A spore suspension of Pyricularia oryzae was sprayed for inoculation over seedlings of a rice plant (variety: Asahi) grown up to the third leaf stage which had been soil cultured in an unglazed pot with a diameter of 9 cm in a green house. After the inoculation, the pot was placed in a humid chamber and maintained at 24°–25° C. under the conditions of a relative humidity of 95–100%. One day after the inoculation, each of test liquids which were diluted to a predetermined concentration was sprayed over the seedlings. Five days after the spraying, the control value and the degree of chemical injury were determined similarly to Experimental Example 1, with the results shown in Table 3 below.

TABLE 3

(Effect of curative treatment to blast)

| Compound No. | Concentration of sprayed liquid (ppm) | Control Value (%) | Degree of chemical injury |
|---|---|---|---|
| 1 | 200 | 100 | 0 |
| 2 | " | 100 | 0 |
| 3 | " | 98 | 0 |
| 4 | " | 100 | 0 |
| 5 | " | 100 | 0 |
| 6 | " | 88 | 0 |
| 7 | " | 100 | 0 |
| 9 | " | 100 | 0 |
| 11 | " | 100 | 0 |
| 12 | " | 100 | 0 |
| 13 | " | 100 | 0 |
| 14 | " | 92 | 0 |
| 15 | " | 100 | 0 |
| 16 | " | 100 | 0 |
| 17 | " | 100 | 0 |
| 23 | " | 86 | 0 |
| 24 | " | 84 | 0 |
| 27 | " | 100 | 0 |
| 28 | " | 98 | 0 |
| 29 | " | 100 | 0 |
| 30 | " | 100 | 0 |
| 31 | " | 84 | 0 |
| 32 | " | 93 | 0 |
| 33 | " | 82 | 0 |
| 34 | " | 100 | 0 |

TABLE 3-continued (Effect of curative treatment to blast)

| Compound No. | Concentration of sprayed liquid (ppm) | Control Value (%) | Degree of chemical injury |
|---|---|---|---|
| 35 | " | 95 | 0 |
| 36 | " | 99 | 9 |
| 37 | " | 81 | 0 |
| 38 | " | 100 | 0 |
| 39 | " | 100 | 0 |
| 40 | " | 100 | 0 |
| 41 | " | 100 | 0 |
| 42 | " | 100 | 0 |
| 43 | " | 86 | 0 |
| 44 | " | 92 | 0 |
| 45 | " | 90 | 0 |
| 46 | " | 99 | 0 |
| 47 | " | 100 | 0 |
| Comparative chemical 1 | " | 70 | 5 |
| Comparative chemical 2 | " | 71 | 5 |
| Comparative chemical 3 | " | 70 | 5 |
| Comparative chemical 4 | 480 | 80 | 0 |
| Non-treated plot | — | 0 | — |

In the above table, the comparative chemicals 1, 2, 3 and 4 are those indicated in Experimental Example 1, respectively.

Experimental Example 3 (Test for Effect of Controlling Rice Brown Spot)

Each of test liquids diluted to a predetermined concentration was sprayed over seedlings of a rice plant (variety: Asahi) grown up to the fourth leaf stage which had been soil cultured in an unglazed pot with a diameter of 9 cm in a green house. One day after the spraying, a conidiospore suspension of Cochliobolus miyabeanus were sprayed over seedlings for inoculation. Five days after the inoculation, the number of lesions per leaf of the fourth leaf stage was checked and a control value was calculated from the following equation. The degree of chemical injury against the rice plant was checked similarly to Experimental Example 1. The test results are shown in Table 4.

TABLE 4

Control Value (%) =

$$\left(1 - \frac{\text{Number of lesions in sprayed plot}}{\text{Number of lesions in non-sprayed plot}}\right) \times 100$$

(Effect of controlling brown spot)

| Compound No. | Concentration of sprayed liquid (ppm) | Control Value (%) | Degree of chemical injury |
|---|---|---|---|
| 1 | 500 | 99 | 0 |
| 2 | " | 94 | 0 |
| 3 | " | 100 | 0 |
| 4 | " | 85 | 0 |
| 5 | " | 100 | 0 |
| 6 | " | 100 | 0 |
| 7 | " | 100 | 0 |
| 8 | " | 61 | 0 |
| 9 | " | 100 | 0 |
| 10 | " | 60 | 0 |
| 11 | " | 100 | 0 |
| 12 | " | 100 | 0 |
| 13 | " | 100 | 0 |
| 14 | " | 94 | 0 |
| 15 | " | 81 | 0 |
| 16 | " | 100 | 0 |

TABLE 4-continued

Control Value (%) =

$$\left(1 - \frac{\text{Number of lesions in sprayed plot}}{\text{Number of lesions in non-sprayed plot}}\right) \times 100$$

(Effect of controlling brown spot)

| Compound No. | Concentration of sprayed liquid (ppm) | Control Value (%) | Degree of chemical injury |
|---|---|---|---|
| 17 | " | 100 | 0 |
| 18 | " | 90 | 0 |
| 20 | " | 91 | 0 |
| 21 | " | 77 | 0 |
| 22 | " | 100 | 0 |
| 23 | " | 84 | 0 |
| 24 | " | 89 | 0 |
| 26 | " | 100 | 0 |
| 28 | " | 100 | 0 |
| 29 | " | 100 | 0 |
| 30 | " | 87 | 0 |
| 32 | " | 76 | 0 |
| 33 | " | 82 | 0 |
| 34 | " | 98 | 0 |
| 35 | " | 92 | 0 |
| 36 | " | 100 | 0 |
| 37 | " | 93 | 0 |
| 38 | " | 87 | 0 |
| 39 | " | 78 | 0 |
| 40 | " | 81 | 0 |
| 41 | " | 100 | 0 |
| 42 | " | 100 | 0 |
| 43 | " | 94 | 0 |
| 44 | " | 91 | 0 |
| 45 | " | 88 | 0 |
| 46 | " | 99 | 0 |
| 47 | " | 90 | 0 |
| Comparative Chemical 1 | " | 75 | 5 |
| Comparative Chemical 2 | " | 73 | 5 |
| Comparative Chemical 3 | " | 70 | 5 |
| Comparative Chemical 4 | " | 90 | 0 |
| Non-treated plot | — | 0 | — |

In the above table, the comparative chemical 1, 2 and 3 are the same as in Experimental Example 1 and the comparative chemical 4 is a commercially available bactericide (called triazine) containing 2,4-dichloro-6-(O-chloroanilino)-1,3,5-triazine.

Experimental Example 4 (Test for Effect of Controlling Cucumber Powdery Mildew)

10 ml of each of test liquids diluted to a predetermined concentration was sprayed over seedlings of a cucumber plant (variety: Sagami Hanpaku) grown up to the first leaf stage which has been soil cultured in an unglazed pot with a diameter of 9 cm in a green house. After allowing to stand overnight, the seedlings were sprayed for inoculation with a spore suspension of Sphaerotheca friliginea. Ten days after the inoculation, the rate of a lesion area (%) was checked and a control value was evaluated from the following equation. The degree of chemical injury against a cucumber plant was determined in the same manner as in Experimental Example. The test results are shown in Table 5 below.

TABLE 5

Control Value (%) =

$$\left(1 - \frac{\text{Rate of lesion area in sprayed plot}}{\text{Rate of lesion area in non-sprayed plot}}\right) \times 100$$

(Effect of controlling powdery mildew)

| Compound No. | Concentration of sprayed liquid (ppm) | Control value (%) | Degree of chemical injury |
|---|---|---|---|
| 1 | 200 | 90 | 0 |
| 2 | " | 88 | 0 |
| 3 | " | 94 | 0 |
| 4 | " | 90 | 0 |
| 5 | " | 85 | 0 |
| 6 | " | 100 | 0 |
| 7 | " | 100 | 0 |
| 8 | " | 78 | 0 |
| 9 | " | 100 | 0 |
| 11 | " | 90 | 0 |
| 12 | " | 100 | 0 |
| 13 | " | 100 | 0 |
| 14 | " | 100 | 0 |
| 15 | " | 91 | 0 |
| 17 | " | 100 | 0 |
| 20 | " | 78 | 0 |
| 21 | " | 86 | 0 |
| 23 | " | 82 | 0 |
| 24 | " | 80 | 0 |
| 25 | " | 75 | 0 |
| 28 | " | 100 | 0 |
| 29 | " | 100 | 0 |
| 30 | " | 92 | 0 |
| 31 | " | 77 | 0 |
| 32 | " | 93 | 0 |
| 33 | " | 94 | 0 |
| 34 | " | 100 | 0 |
| 35 | " | 100 | 0 |
| 36 | " | 93 | 0 |
| 37 | " | 100 | 0 |
| 38 | " | 100 | 0 |
| 39 | " | 100 | 0 |
| 40 | " | 97 | 0 |
| 41 | " | 94 | 0 |
| 42 | " | 92 | 0 |
| 43 | " | 82 | 0 |
| 44 | " | 94 | 0 |
| 45 | " | 91 | 0 |
| 46 | " | 83 | 0 |
| 47 | " | 79 | 0 |
| Comparative Chemical 1 | " | 53.2 | 1 |
| Comparative Chemical 2 | " | 48.3 | 1 |
| Comparative Chemical 3 | " | 95.8 | 0 |
| Non-treated plot | — | 0 | — |

In the above table, the comparative chemicals 1 and 2 correspond to the comparative chemicals 1 and 3 of Experimental example 1, respectively, and the comparative chemical 3 is a commercially available liquid (Milcurb) containing 2-dimethylamino-4-methyl-5-butyl-6-hydroxypyrimidine.

Experimental Example 5 (Test for Antimicrobial Activity Against Various Plant Phathogenic Fungi)

1 ml of an acetone solution of each of test compounds and 20 ml of the PDA medium (50° C.) to prepare media containing the chemical in different concentrations, followed by charging into a petri dish with a diameter of 9 cm where it was solidified flat. On the central portion of the chemical-containing medium was inoculated a fungus-containing medium a piece of ager black-containing mycelia which was obtained by punching by means of a cork borer the tip portion of mycelia of each test fungus which had been cultured in advance in the PDA medium, followed by cultivating at 24° C. Two to six days after the cultivation, the diameter of the mycelia was measured and mycelium growth inhibiting rate was calculated from a comparison with that of a non-treated plot. The mycelium growth inhibiting rate was plotted on a logarithmic probability paper to determine an $ED_{50}$ value. The test results are shown in Table 6 below.

TABLE 6

Antimicrobial activity against various plant pathogenic fungi

| Plant pathogenic fungi | $ED_{50}$ value (ppm) Compound No. | | | | | | |
|---|---|---|---|---|---|---|---|
| | 4 | 27 | 32 | 35 | 38 | 41 | 42 |
| Glomerella cingulata | 4.1 | 6.7 | 7.0 | 9.6 | 7.3 | 4.1 | 4.0 |
| Diaporthe citri | 2.7 | 2.9 | 4.0 | 4.6 | 3.8 | 2.0 | 2.7 |
| Endothia parasitica | 1.9 | 6.3 | 7.5 | 6.8 | 6.2 | 4.6 | 3.8 |
| Mycosphaerella melonis | 5.2 | 4.6 | 1.8 | 2.0 | 4.0 | 0.7 | 0.9 |
| Cochliobolus miyabeanus | 4.6 | 2.2 | 3.8 | 4.3 | 2.8 | 1.4 | 1.8 |
| Sclerotinia sclerotiorum | 3.2 | 4.8 | 5.5 | 6.1 | 3.6 | 3.8 | 5.2 |
| Sclerotinia fructigena | 0.4 | 1.4 | 0.9 | 0.7 | 1.6 | 1.5 | 2.1 |
| Pellicularia sasakii | 1.2 | 1.0 | 1.5 | 1.3 | 1.2 | 1.1 | 2.0 |
| Penicillium digitatum | 1.3 | 1.2 | 0.6 | 0.8 | 1.4 | 1.1 | 2.0 |
| Botrytis cinerea | 6.5 | 9.8 | 13.8 | 9.6 | 8.8 | 4.5 | 3.7 |
| Pyricularia oryzae | 0.1 | 0.02 | 0.8 | 0.2 | 0.04 | 0.01 | 0.02 |
| Helminthosporium gramineum | 2.4 | 3.6 | 7.5 | 6.3 | 3.2 | 2.8 | 5.2 |
| Alternaria padwikii | 1.2 | 1.9 | 1.2 | 1.0 | 1.7 | 0.7 | 0.7 |
| Fusarium nivale | 5.3 | 2.8 | 2.3 | 2.6 | 2.7 | 0.2 | 2.0 |
| Curvularia sp. | 0.7 | 1.6 | 1.6 | 1.8 | 1.5 | 1.6 | 1.4 |
| Phoma lingam | 2.1 | 3.7 | 5.3 | 4.6 | 2.7 | 2.6 | 3.2 |
| Phizoctonia solani | 1.1 | 1.1 | 2.4 | 2.8 | 2.0 | 1.4 | 1.3 |

What we claim is:

1. A pyrazolylpyrimidine of the formula

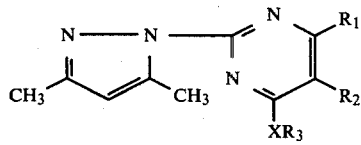

wherein $R_1$ is hydrogen or $C_{1-6}$ alkyl, $R_2$ is hydrogen or $C_{1-4}$ alkyl, X is oxygen or sulfur and $R_3$ is phenyl or phenyl substituted with from 1 to 3 substituents selected from the group consisting of halogen, $C_1$-$C_4$ alkyl, methoxy, methylthio, cyano, nitro, trifluoromethyl and carbethoxy; provided that when $R_1$ is $C_{1-6}$ alkyl, $R_2$ is hydrogen and X is oxygen, $R_3$ is said substituted phenyl, and excluding pyrazolylpyrimidines where $R_1$ is $C_{1-6}$ alkyl, $R_2$ is $C_{1-4}$ alkyl and X is sulfur.

2. A fungicide composition comprising as active ingredient, a fungicidally effective amount of a pyrazolylpyrimidine of the formula

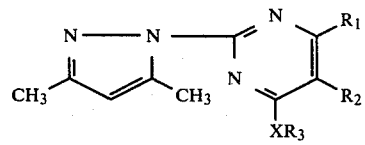

wherein $R_1$ is hydrogen or $C_{1-6}$ alkyl, $R_2$ is hydrogen or $C_{1-4}$ alkyl, X is oxygen or sulfur and $R_3$ is lower alkyl, phenyl or phenyl substituted with from 1 to 3 substituents selected from the group consisting of halogen, $C_{1-4}$ alkyl, methoxy, methylthio, cyano, nitro, trifluoromethyl and carbethoxy; provided that when $R_1$ is $C_{1-6}$ alkyl, $R_2$ is $C_{1-4}$ alkyl and X is sulfur, $R_3$ is ethyl or when $R_1$ is $C_{1-6}$ alkyl, $R_2$ is hydrogen and X is oxygen, $R_3$ is said substituted phenyl in a suitable carrier.

* * * * *